US011808775B2

(12) United States Patent
Fu et al.

(10) Patent No.: US 11,808,775 B2
(45) Date of Patent: Nov. 7, 2023

(54) CATHINONE TEST

(71) Applicant: University of Technology Sydney, Ultimo (AU)

(72) Inventors: Shanlin Fu, Ultimo (AU); Morgan Philp, Ultimo (AU); Ronald Shimmon, Ultimo (AU)

(73) Assignee: University of Technology Sydney

( * ) Notice: Subject to any disclaimer, the term of this patent is extended or adjusted under 35 U.S.C. 154(b) by 695 days.

(21) Appl. No.: 16/763,086

(22) PCT Filed: Nov. 15, 2018

(86) PCT No.: PCT/AU2018/051221
§ 371 (c)(1),
(2) Date: May 11, 2020

(87) PCT Pub. No.: WO2019/095011
PCT Pub. Date: May 23, 2019

(65) Prior Publication Data
US 2020/0348320 A1 Nov. 5, 2020

(30) Foreign Application Priority Data

Nov. 15, 2017 (AU) .............................. 2017904618

(51) Int. Cl.
*G01N 33/94* (2006.01)
*G01N 33/18* (2006.01)
*G01N 33/52* (2006.01)

(52) U.S. Cl.
CPC ......... *G01N 33/94* (2013.01); *G01N 33/1813* (2013.01); *G01N 33/52* (2013.01)

(58) Field of Classification Search
CPC ...................................................... G01N 33/94
See application file for complete search history.

(56) References Cited

U.S. PATENT DOCUMENTS 8,128,805 B2 * 3/2012 Vaarkamp .............. C10G 49/08
208/143

OTHER PUBLICATIONS

Morgan, Philp, The development of novel optical screening tests for the presumptive identification of New Psychoactive Substances (NPS) in seized illicit materials, Jul. 25, 2018, pp. 1-369, XP55804351, Retrieved from the Internet: URL:https://opus.lib.uts.edu.au/bitstream/10453/128009/2/02whole.pdf [retrieved on May 14, 2021].
Anonymous: "Catalysis", Wikipedia, Nov. 10, 2017, pp. 1-11 , XP55804444, Retrieved from the Internet: URL:https://en.wikipedia.org/w/index.php?title=Catalysis&oldid=809699705 [retrieved on May 14, 2021].
European Search Report for corresponding Application No. EP18877543 dated May 17, 2021, pp. 1-7.

(Continued)

*Primary Examiner* — Benjamin J Packard
(74) *Attorney, Agent, or Firm* — The Belles Group, P.C.

(57) ABSTRACT

A method of detecting the presence of a cathinone moiety in a sample, such as a suspected illicit drug sample, which comprises contacting the sample with a solution comprising neocuproine, a source of copper(II) and a catalyst and observing a colour change, where present, that correlates with the presence of cathinone. The method is operable at environmental temperature. Mechanical elements may be employed to accelerate the colour change if desired.

17 Claims, 7 Drawing Sheets

(56) References Cited

OTHER PUBLICATIONS

Al-Obaid et al., "Determination of (S)(-)-cathinone by spectrophotometric detection," Journal of Pharmaceutical and Biomedical Analysis, 17 (1998) pp. 321-326.
Philp, M. et al., "Development and validation of a presumptive color spot test method for the detection of synthetic cathinones in seized illicit materials," Forensic Chemistry, 1, 2016, pp. 39-50.
International Search Report for corresponding Application No. PCT/AU2018/051221 dated Jan. 8, 2019, pp. 1-3.

* cited by examiner

CATHINONE TEST

CROSS-REFERENCE TO RELATED PATENT APPLICATIONS

The present application is a U.S. national stage application under 35 U.S.C. § 371 of PCT Application No. PCT/AU2018/051221, filed Nov. 15, 2018, which claims priority to Australian Patent Application No. 2017904618, filed Nov. 15, 2017. The disclosures of the aforementioned priority applications are incorporated herein by reference in their entireties.

FIELD OF THE INVENTION

The invention relates to tests for the determination of illicit substances. In particular, the invention relates to tests for the detection of drugs of the cathinone family. The invention also relates to kits and devices for the detection of cathinones.

BACKGROUND

The present-day illicit drug trade is a large, lucrative, global industry. Technological advances and the ingenuity of rogue chemists continues to present ongoing challenges for law enforcement authorities and for scientists and engineers developing the technology to support them.

In recent years, the recreational drug market has seen an increase in the abuse of Drug Analogues and New Psychoactive Substances, known collectively as (DANPS). DANPS are substances that are structurally or functionally similar to a prohibited or scheduled parent compound. They are of great concern due to the number and diversity of compounds involved and a lack of knowledge about their mode of action, side effects and toxicity. DANPS are often deliberately mislabelled by suppliers in order to avoid legal barriers (cathinones are often labelled "bath salts"), or they are presented to customers as "legal" alternatives to illicit drugs.

One particular class of DANPS are the cathinones. Cathinones are psychoactive compounds which can be a relatively inexpensive alternative to more established drugs. Synthetic cathinones as a class have accounted for the highest proportion of DANPS seizures in Australia since 2008. In 2013-14, the number of synthetic cathinone seizures made up 34.8 percent of those analysed. Similar trends have been observed elsewhere in the world, for instance, in Europe.

The general chemical structure of synthetic cathinones is shown below.

$R_1$, $R_2$, $R_3$ and $R_4$ can be modified independently to provide and an almost unlimited number of cathinone-type substances.

In order to prosecute offenders, it is necessary to be able to identify the drugs involved. Like most small molecules, cathinones can be identified by techniques such as Gas Chromatography-Mass Spectrometry (GC-MS) and High Performance Liquid Chromatography-Mass Spectrometry (HPLC-MS) and comparison with reference libraries and reference standards. These techniques combine separation power with spectroscopic analysis and are considered to be the 'gold standard' for routine analysis. Although these tests are highly reliable, such instruments are not ideal for high throughput sample analysis owing to their high cost of running, the need for trained personnel, lengthy analysis times, and optimization and maintenance requirements.

The large number of illicit drug seizures means that simple, rapid, inexpensive, and accurate field tests are highly desirable.

Presumptive screening tests are designed to provide an indication of the presence or absence of certain drug classes in a test sample. They need to be simple to carry out and sufficiently reliable such that they can form the basis for detaining suspects until definitive tests can be completed.

Colour 'spot' tests are a particularly useful type of field test that result in a colour change when applied to a sample containing a drug of interest. The chemical reaction occurring between the colour reagent and the drug of interest provides a very rapid first line screening tool which can, in some cases, be quite selective.

The increase in prevalence of synthetic cathinones in illicit drug seizures has resulted in a number of commercially available test kits for synthetic cathinones being developed. However, these tests often employ hazardous substances, demonstrate a lack of selectivity toward the cathinone class, or have not been screened on a large number of available synthetic cathinone substances. Inadequate screening tests can result in new psychoactive substances going undetected or being incorrectly identified.

Cathinone itself is a naturally occurring psychoactive alkaloid found in the Khat plant, which is native to Eastern Africa. Cathinone from the Khat plant was described by Al-Obaid earlier in *J. Pharm. Biomed. Anal.* 17 (1998) 321-326. Philp et al in *Forensic Chemistry* 1 (2016) 39-50 describe a test regime that could be used to detect a range of synthetic cathinones. However, although this test showed good specificity, it was inherently unsuitable for field use as it required a heating step at 80° C. for at least 2 minutes in order to develop a suitable colour. Without heating, the test in Philp et al required around 24 hours to develop a suitable colour. The use of either a heating step or a lengthy time frame is unsuitable for field tests and is unlikely to be used by field officers.

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

SUMMARY

According to a first aspect the invention provides a method of detecting the presence of a cathinone moiety in a sample, the method comprising the steps of contacting the sample with a solution comprising neocuproine, a source of copper(II), a buffer solution, and a catalyst and observing a colour change, where present, that correlates with the presence of cathinone, and wherein the method takes place at environmental temperature.

According to a second aspect, the invention provides a method of detecting the presence of a cathinone moiety in a sample, the method comprising the steps of:

i. contacting the sample with a solution comprising neocuproine, a source of copper(II), and a plurality of mechanical elements;
ii. agitating the mechanical elements to provide friction therebetween and observing a colour change, where present, that correlates with the presence of cathinone, and wherein the method takes place at environmental temperature.

According to a third aspect, the invention provides a method of detecting the presence of a cathinone moiety in a sample, the method comprising the steps of:
i. contacting the sample with a solution comprising neocuproine, a source of copper(II), a catalyst and a plurality of mechanical elements;
ii. agitating the mechanical elements to provide friction therebetween; and observing a colour change, where present, that correlates with the presence of cathinone, and wherein the method takes place at environmental temperature.

According to a fourth aspect, the invention provides a test reagent for detecting the presence of a cathinone moiety in a sample, the reagent comprising neocuproine and a source of copper(II).

Preferably, the colour change is observed at environmental temperature within 10 minutes, more preferably within 5 minutes and most preferably within 2 minutes.

The solution is preferably an aqueous solution.

The buffer is preferably a mild acidic buffer to keep the pH in the range 3-6 or even 4-5. An acetate buffer, such as sodium acetate is preferred.

The sample, the neocuproine, the source of copper(II), the catalyst and the buffer are added in any order or may be added simultaneously.

Preferably, the source of copper(II) is copper nitrate. Preferably the buffer is sodium acetate.

The catalyst for preference is selected from the group consisting of alkali metal halides and surface active catalysts, more preferably from the group consisting of lithium fluoride, potassium fluoride, potassium chloride, silica gel, molecular sieves, Amberlyst A-21 (a weak base ion exchange resin). Most preferably the catalyst is lithium fluoride, potassium chloride or silica gel.

In one embodiment, the mechanical elements are beads, preferably the beads are selected from glass beads, polyethylene balls and polyvinyl acetate spheres and silica gel particles. Glass beads are most preferred. Preferably, the method is carried out in a malleable container, for example, a bag.

The methods of the present invention may also include the use of a discrete organic phase. In one embodiment, the discrete organic phase is denser than the aqueous phase. In that case, the organic phase may be, for example, dichloromethane or chloroform. In another embodiment, the organic phase is less dense than the aqueous phase. In that case, the organic phase may be a hydrocarbon solvent, including but not limited to hexane or heptane for example, or it may for instance be ethyl acetate.

Preferably, the organic phase has a volume less than a volume of the aqueous phase. In some embodiments, the method takes place in a vessel having a reduced or tapering cross section at a lower portion of the vessel. In other embodiments, non-tapered vials, such as GC vials, may be used. Those skilled in the art will readily be able to select a suitable vial type based on the specific intended use.

In the present invention, the sample may be an unknown drug sample, or the sample may be a biological fluid including, for example saliva, blood or urine.

The method of the present invention may be useful, for instance, as a presumptive test for a suspected illicit substance, a presumptive test for a suspected overdose or a presumptive test in sport or workplace testing.

According to a fifth aspect, the invention provides a kit for the detection of a cathinone moiety, the kit comprising the test reagent of the fourth aspect. The kit may further comprise a colour standard or comparison chart.

According to a sixth aspect, the invention provides a strip for the detection of cathinone, the strip comprising a fibrous or paper substrate and deposited thereon an intimate mixture of neocuproine a source of copper(II) and sodium acetate.

The invention also provides devices for carrying out the methods of the present invention.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "environmental temperature" refers to the range of temperatures that would be expected to be present when field officers are conducting the presumptive tests, which would be any range of temperatures where humans can survive. Examples of environmental temperature ranges are, for instance, the range −20° C. to 45° C., 0° C. to 45° C. or 1° C. to 40° C.

DESCRIPTION

The chemical basis for the present test is based upon the reduction-oxidation reaction between the cathinone moiety and a copper(II)-neocuproine complex to form the highly coloured copper(I)-neocuproine chelate complex.

The proposed chemical basis for the reaction is shown below:

2,9-Dimethyl-1,10-phenanthroline (neocuproine) is reacted with a source of copper(II), such as copper nitrate in the presence of a buffer, such as sodium acetate. The resultant product is the proposed copper(II)-neocuproine complex. The copper(II)-neocuproine complex is a light blue colour but otherwise there is little absorbance in the visible part of the UV spectrum.

Figure 1:
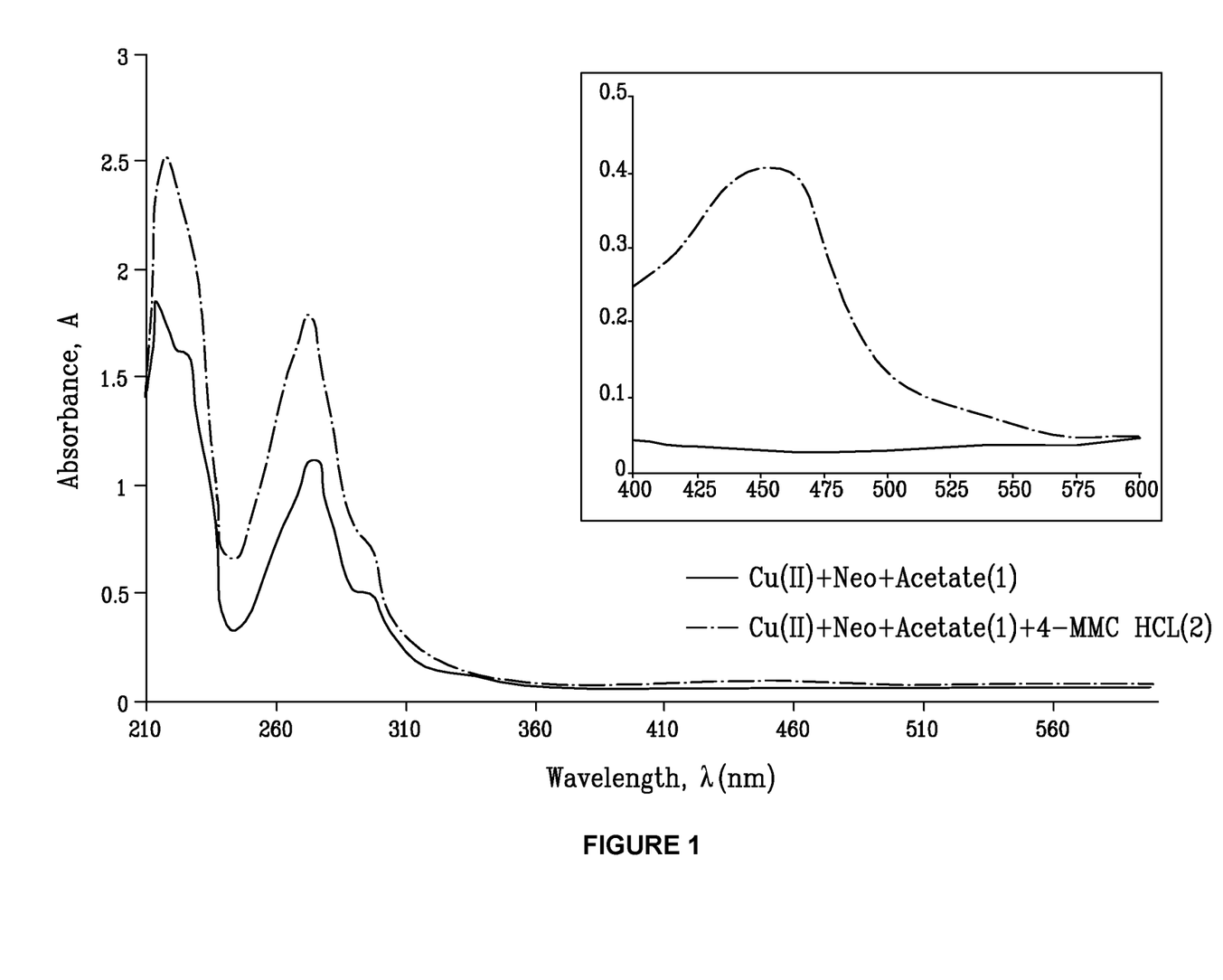
FIG. 1 shows the UV visible spectrum of the complexes of the present invention.

The copper(II)-neocuproine complex, when contacted with a suitable reductant, such as the cathinone moiety, in the presence of heat, is oxidised to a copper(I)-neocuproine complex. The copper(I)-neocuproine complex is strongly orange coloured, having a significant absorbance peaking at around 453 nm. Thus, there is a very clear indication of the different species present. The UV visible spectrum for the copper(II)-neocuproine and the reduced, cathinone complexed form is shown in FIG. 1. This clearly illustrating the dramatic increase in absorbance at around 453 nm that takes place upon cathinone complexation.

A very important factor for tests seeking to establish a presumptive test is their level of reliability. It is important that the test does not have too many false negatives (in this case, missing many cathinone derivatives), or too many false positives (leading to the detention of too many suspects that will ultimately not lead to convictions).

As shown in Philp et al, the neocuproine test was highly specific for cathinones.

The test in Philp et al against 44 cathinone samples showed a positive result in 39 of those cases. That is a positive detection rate of 89%.

The test was carried out using the methods of the present invention (catalyst and discrete organic phase) against the same 44 cathinone samples and all of those showed a positive result. That is a positive detection rate of 100%. Thus, the methods of the present invention enabled a significantly higher detection range than previously observed. The following table illustrates the range of cathinones tested:

| CATHINONE | RESULT |
|---|---|
| 1-(4-methoxyphenyl)-2-(1-pyrrolidinyl)-1-propanone HCl (MOPPP) | + |
| 1-phenyl-2-methylamino-pentan-1-one HCl | + |
| 2,3-dimethylmethcathinone HCl (2,3-DMMC) | + |
| 2,3-dimethylmethcathinone HCl (2,3-DMMC) | + |
| 2,4,5-trimethylmethcathinone HCl (2,4,5-TMMC) | + |
| 2,4-dimethylmethcathinone HCl (2,4-DMMC) | + |
| 2-fluoromethcathinone HCl (2-FMC) | + |
| 2-benzylamino-1-(3,4-methylenedioxyphenyl)-1-butanone HCl (BMDB) | + |
| 2-methylmethcathinone HCl (2-MMC) | + |
| 3,4-methylenedioxy-α-pyrrolidinobutiophenone HCl | + |
| 3,4-dimethylmethcathinone HCl (DMMC) | + |
| 3,4-methylenedioxymethcathinone HCl (MDMC) | + |
| 3,4-methylenedioxy-N,N-dimethylcathinone HCl | + |
| 3,4-methylenedioxypyrovalerone HCl (MDPV) | + |
| 3-bromomethcathinone HCl (3-BMC) | + |
| 3-fluoromethcathinone HCl (3-FMC) | + |
| 3-methylmethcathinone HCl (3-MMC) | + |
| 4-bromomethcathinone HCl (4-BMC) | + |
| 4-fluoromethcathinone HCl | + |
| 4-methoxymethcathinone HCl | + |
| 4-methylethylcathinone HCl | + |
| 4-methylmethcathinone HCl (4-MMC) | + |
| 4-methyl-N-benzylcathinone HCl (4-MBC) | + |
| 4-methyl-pyrrolidinopropiophenone HCl | + |
| 4-methyl-α-pyrrolidinobutiophenone HCl | + |
| cathinone HCl (bk-amphetamine) | + |
| dibutylone HCl (bk-DMBDB) | + |
| iso-ethcathinone HCl | + |
| methcathinone HCl | + |
| methylenedioxy-α-pyrrolidinopropiophenone HCl | + |
| N,N-diethylcathinone HCl | + |
| N,N-dimethylcathinone HCl | + |
| naphthylpyrovalerone HCl (naphyrone) | + |
| N-ethyl-3,4-methylenedioxycathinone HCl | + |
| N-ethylbuphedrone HCl | + |
| N-ethylcathinone HCl | + |
| pentylone HCl | + |

| CATHINONE | RESULT |
|---|---|
| pyrovalerone HCl | + |
| a-dimethylaminobutyrophenone | + |
| α-dimethylaminopentiophenone HCl | + |
| α-ethylaminopentiophenone HCl | + |
| α-pyrrolidinobutiophenone HCl (α-PBP) | + |
| α-pyrrolidinopentiophenone HCl | + |
| α-pyrrolidinopropiophenone HCl | + |
| β-keto-N-methyl-3, 4-benzodioxyolylbutanamine HCl (bk-MBDB) | + |
| Methylone + 4-FMC | + |
| MMC + benzocaine | + |
| MMC + caffeine | + |
| MMC + codeine phosphate | + |
| MMC + ephedrine | + |
| MMC + 4-FMC | + |
| MMC + lactose | + |
| MMC + methylone | + |

In addition to being able to reliably identify the class of substances targeted, a presumptive test should minimise the amount of false positives, i.e. should not give positive results on other substances. This is particularly the case in drug tests, where target substances are often adulterated with a variety of household chemicals.

The neocuproine test for cathinones was also carried out against a range of other recreational drugs. A sample of 44 drugs tested showed only 3 false positives.

| DRUG | RESULT |
|---|---|
| (−)-ephedrine HCl | − |
| (−)-methylephedrine HCl | − |
| (+)-cathine HCl | − |
| (+/−)-3,4-methylenedioxyamphetamine (MDA) HCl | − |
| (+/−)-N-methyl-3,4-methylenedioxyamphetamine (MDMA) HCl | − |
| (+/−)-methamphetamine HCl | − |
| (+/−)-N-ethyl-3,4-methylenedioxyamphetamine (MDEA) HCl | − |
| (+/−)-N-methyl-1-(3,4-methylenedioxyphenyl)-2-butylamine HCl | − |
| (+/−)-phenylpropanolamine | − |
| (2S*,3R*)-2-methyl-3-[3,4-(methylenedioxy)phenyl]glycidic acid methyl ester | − |
| 1-(3-chlorophenyl)piperazine (mCPP) HCl | − |
| 1-[3-(trifluoromethyl)phenyl]piperazine (TFMPP) HCl | + |
| 1-benzylpiperazine (BZP) HCl | − |
| 2,5-dimethoxy-4-iodophenylethylamine HCl | − |
| 2,5-dimethoxy-4-methylamphetamine | − |
| 2,5-dimethoxy-4-propylthio-phenylethylamine | − |
| 2,5-dimethoxyamphetamine | − |
| 2-bromo-4-methylpropiophenone | − |
| 2-fluoroamphetamine | − |
| 2-fluoromethamphetamine | − |
| 3,4-dimethoxyamphetamine | − |
| 3,4-methylenedioxyphenyl-2-propanone (MDP2P) | − |
| 4-bromo-2,5-dimethoxyamphetamine HCl | − |
| 4-bromo-2,5-dimethoxyphenethylamine HCl | − |
| 4-fluoroamphetamine | − |
| 4-fluorococaine HCl | − |
| 4-fluoromethamphetamine | − |
| 4-hydroxyamphetamine | − |
| 4-methoxyamphetamine (PMA) | − |
| 4-methoxymethamphetamine (PMMA) | − |
| 4-methylmethamphetamine | − |
| 4-methylpropiophenone | + |
| 5-methoxy-N,N-diallyltryptamine | + |
| amphetamine sulphate | − |
| cocaine HCl | − |
| dimethamphetamine (DMA) | − |
| gamma-hydroxy butyrate | − |
| heroin HCl | − |
| ketamine | − |
| methoxetamine HCl | − |
| methylamine HCl | − |
| phencyclidine HCl | − |
| phentermine | − |
| triethylamine | − |

The neocuproine test was also carried out against a range of bulking agents and adulterants commonly used. Again, out of 35 commonly used adulterants, only 5 gave a false positive test.

| ADULTERANT | RESULT |
|---|---|
| artificial sweetener | – |
| ascorbic acid | + |
| benzocaine | – |
| benzoic acid | – |
| boric acid | – |
| brown sugar | – |
| caffeine | – |
| calcium chloride | – |
| caster sugar/icing sugar | – |
| citric acid | – |
| codeine phosphate | + |
| dimethylsulfone | – |
| ephedrine HCl | – |
| glucose | – |
| glycine | – |
| Lactose | – |
| L-cysteine | + |
| levamisole | – |
| L-glutathione | + |
| magnesium sulphate | – |
| maltose | – |
| mannitol | – |
| O-acetylsalicylic Acid | – |
| paracetamol | + |
| phenethylamine | – |
| phenolphthalein | – |
| potassium carbonate | – |
| protein powder | – |
| self-raising/plain flour | – |
| sodium carbonate | – |

-continued

| ADULTERANT | RESULT |
|---|---|
| sodium chloride | – |
| starch/cellulose | – |
| stearic acid | – |
| sucrose | – |
| tartaric acid | – |

Thus, out of a range of 82 non-cathinone compounds tested, only 8 gave false positive results. The neocuproine test thus is able to detect about 100% of cathinones and does not provide a false positive in more than about 10% of substances commonly encountered in drug operations.

Another important factor for presumptive testing, alongside selectivity, is sensitivity. In Philp et al the he neocuproine test, under laboratory conditions, was shown to be capable of visualizing a colour change with just 4 μg of sample present. Accordingly, based on calculations using established principles, this would correspond to an operational detection limit of 40 μg. Of course, if the cathinone was present in much larger amounts, the colour developed much more rapidly.

Using the methods of the present invention, under laboratory conditions, it was shown to be possible to visualize a colour change with just 1 μg of sample present. Based on established principles, this would correspond to an improved operational detection limit of 10 μg.

The colour persisted for around four hours after reaching maximum intensity, which is sufficient for a presumptive test.

The test in Philp et al, when conducted on a small scale, involved the method being performed in a microwell plate using Pasteur pipettes to add drop-sized amounts of reagents. To a pin-head sized amount of seized material was added: Cu(II) ($5.00 \times 10^{-3}$ mol/L, 5 drops), Neocuproine ($5.12 \times 10^{-3}$ mol/L, 2 drops), acetate buffer (2.00 M, 2 drops) and the plate heated for 10 min on a boiling water bath or hotplate. The colour development was then observed.

However, the test disclosed in Philp eta/was unsuitable as a field test because of the requirement that the sample was heated.

The present inventors have found that adaptations of the test described in Philp can result in the test giving a definitive result in two minutes without the need to apply external heating.

It has been found that the addition of certain agents can function to activate or catalyse the reaction and lead to the formation of a coloured complex indicative of cathinone which is fully developed within a few minutes.

The table below shows the identity of the catalyst added to the well and the time taken for a colour change to occur was recorded. Catalyst addition after drug (4-MMC HCl (mephedrone)) and reagents was also tested.

| Catalyst/activator | 5 minutes | 15 minutes |
|---|---|---|
| Lithium fluoride | Pale yellow | Light yellow |
| Potassium fluoride | Light yellow | Light yellow-orange |
| Silica gel | Light yellow | Light yellow-orange |
| Molecular sieves | Light yellow, orange solid | Light yellow, orange solid |
| Amberlyst A-21 | Light yellow, orange solid | Light yellow-orange, orange solid |
| Potassium chloride | Light yellow | Light yellow-orange |

Suitable catalysts included alkali metal halides, such as sodium halides, potassium halides and lithium halides. Alkali metal fluorides, chlorides and bromides were also suitable. Most preferred from this group were lithium fluoride, potassium fluoride and potassium chloride.

Alternatively, catalysts having surface active modifications could also catalyse the reaction, such as silica gel, molecular sieves or Amberlyst A-21. Without wishing to be bound by theory, it is possible that these catalysts allow the coloured product to be adsorbed onto their surface and thus allow for a faster visualisation of any colour change.

Silica gel, KCl and KF showed fastest colour changes.

The use of the heat activators, KF and KCl significantly increased the rate of reaction which led to a faster colour change for all drugs tested (within 5 minutes). In addition, the colour intensity of the results was usually enhanced.

The most sensitive catalysts, those which required the least amount to provide the desired, faster result were LiF, molecular sieves, KCl.

Figure 2:
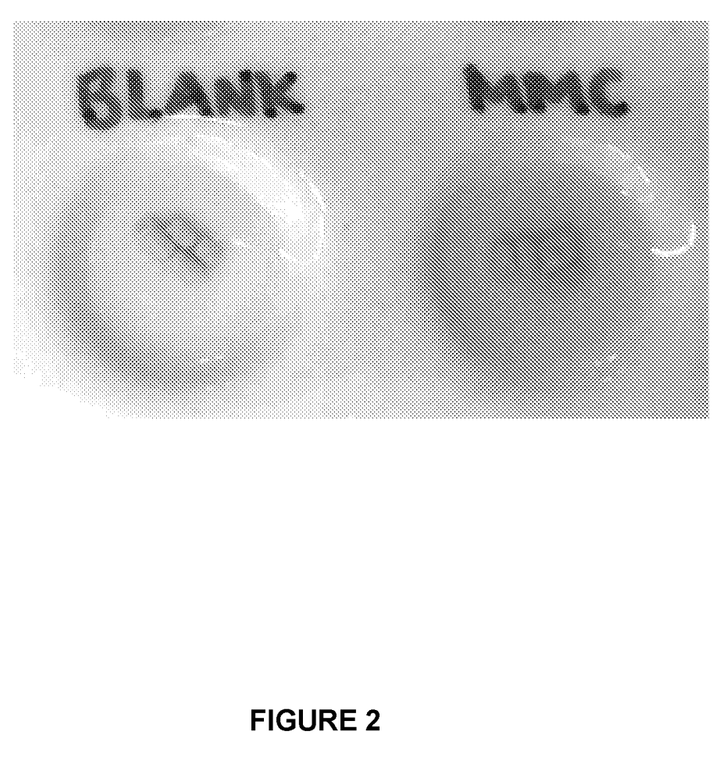
FIG. 2 shows the colour change in molecular sieves evidencing the presence of cathinone.

Molecular sieves absorbed the coloured product and appeared orange. A range of molecular sieves was tested, 3 Å, 4 Å and 5 Å, both activated and unactivated. The unactivated sieves worked significantly better than the activated sieves and the 3 Å sieves, with the smallest pore size, afforded the fastest colour change. FIG. 2 shows the colour change visible with molecular sieves.

In addition to the above, it has also been found that the application of mechanical stimuli to the reaction in the appropriate form can be used to further decrease the time required to achieve a positive result. A moderate degree of mechanical stimulation of the reaction would be acceptable in the context of field test.

Particularly, it has been found that the application of modest amounts of mechanical stimuli, in conjunction with the catalytic effect observed above, can lead to sufficient acceleration of the reaction to produce a clear presumptive result in a field test within the target time of two minutes.

A variety of mechanical elements ("microbeads") were tested, including glass beads, polyethylene balls and polyvinyl acetate spheres, silica gel particles. A hard bead surface is desirable to create more friction. It is also desirable if the mechanical elements are white so as to allow better visualisation of any colour change. Silica gel was quite useful as it could act as both a catalyst and mechanical stimulus with suitable hardness and colour.

Small polyethylene bags were used to contain the microbeads and provide the housing for the colour test 'device'. The cathinone sample, (approximately 100 µg) and reagents were added sequentially, but again the order of addition was found to have no effect on the final outcome.

Gently rubbing the polyethylene bags during the course of the test was found to result in a further reduction in time required to fully develop the colour required for a positive cathinone test. Colour changes without the use of heat were observed in every case where mechanical stimulus was applied to an activated or catalysed test system. However, two combinations were found to be particularly useful—these were:

i) glass beads with KF; and
ii) silica gel and KCl.

Figure 3:
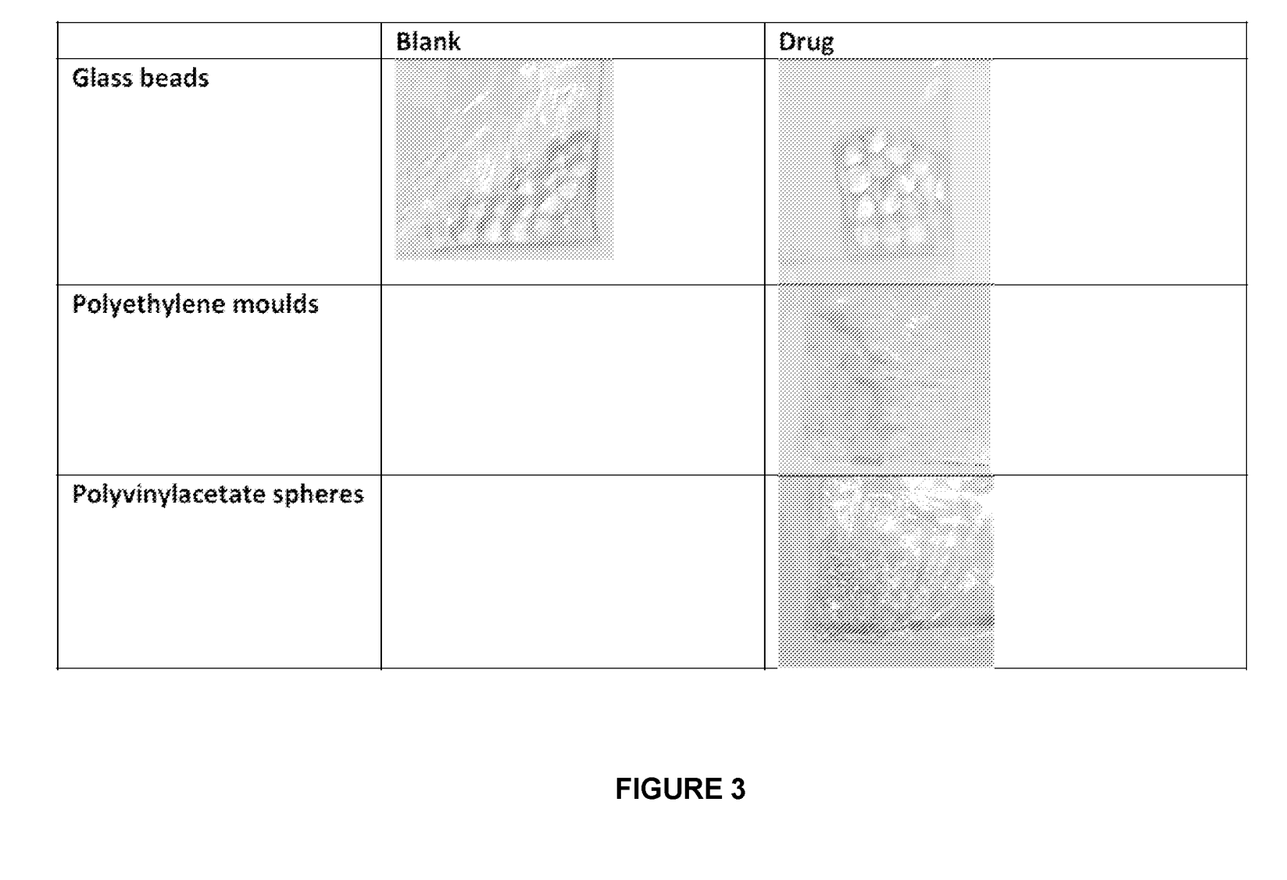
FIG. 3 shows the presence of colour developed by a variety of microbeads.

In both the above cases, colour could be seen to develop after 30 seconds. A useable colour for a presumptive test was present after two minutes and the colour change was fully developed after 5 minutes. FIG. 3 shows the presence of colour developed by a variety of microbeads.

The use of catalysts significantly improved the rate of the reaction at environmental temperature. In combination with a friction mechanism or portable heating device, the colour test time is reduced to under 5 minutes at environmental temperature.

It has also been found possible to intensify the colour change developed by the reaction. This method involves the addition of a small amount of a solvent which is non miscible with the aqueous phase in which the reaction takes place. As the coloured complex develops, it is extracted into the non-miscible (organic phase) which, because of the smaller volume, leads to an increased concentration and increase in colour intensity.

Organic phases can include those that are less dense than water (ether or ethyl acetate) and form a top coloured layer, or those that are more dense than water (chloroform, dichloromethane etc) and form a coloured bottom layer. The addition of the bottom layer is preferred as the colour tends to be easier to observe if concentrated in the bottom of the tube. In addition, the tube can be shaped so as to reduce the effective volume of organic solvent and thereby intensify the colour density. For example, the tube can be tapered so that a small portion of intensely coloured dense solvent sits at the bottom of the tube and can be easily identified. The use of catalysts such as alkali metal halides is also thought to enhance the migration of the coloured complex into the organic phase by a salting out effect. However, the use of an organic phase alone, such as dichloromethane or chloroform, also appears to speed up the development of the colour. Without wishing to be bound by theory, it is possible that migration of the coloured complex into the organic phase assists in driving the equilibrium in the aqueous phase towards the complex.

Figure 4:
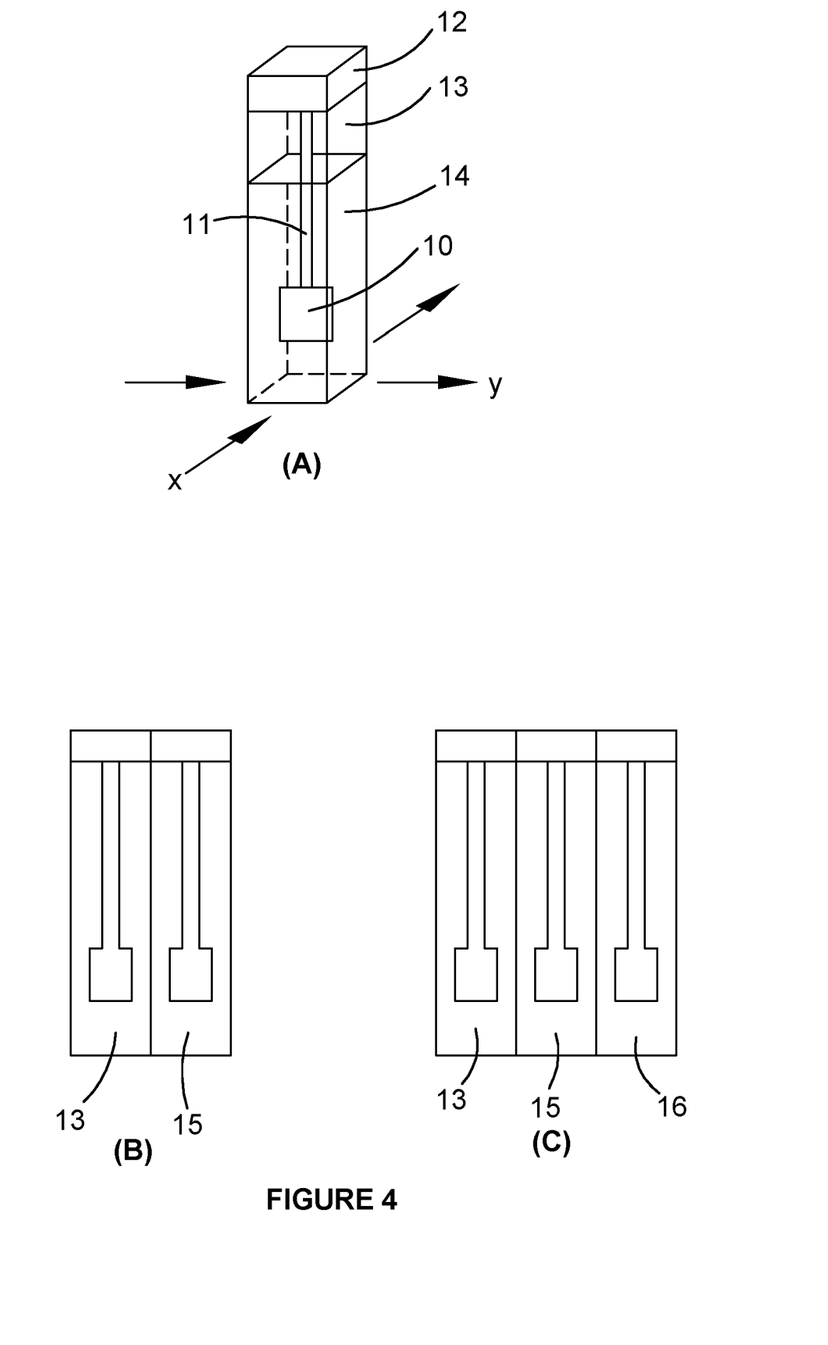
FIG. 4 shows devices suitable for the detection of the colour change.

A device suitable for detection the detection of the colour change is shown in FIG. 4A. A collection swab has an absorbent end section 10 which can be used to collect particles of the suspected drug material for collection. The absorbent portion is mounted on an elongate shaft 11 which connects to the inside of a cuvette lid 12. In use, the absorbent end of the swab is inserted into the cuvette 13 and the cuvette lid is sealingly engaged with the cuvette. The cuvette contains the necessary aqueous reagents 14 to detect cathinone. Upon sealing engagement, the absorbent portion contacts the aqueous reagents and the complexation begins, thereby developing the necessary colour when a cathinone moiety is present. The cuvette as exemplified is of square cross section and has equal optical paths in the x-y plane. This would render the cuvette suitable for both naked eye and instrument detection In FIG. 4B, the cuvette 13 can also have an adjacent reference cuvette 15 integrally formed therewith, which would show the background solution colour and make the colour change more obvious.

In FIG. 4C, the cuvette 13 can also have another chamber 16 attached in proximity thereto which contains no reagents to allow for simultaneous collection and retention of a portion of the sample for further analysis in the event that the validity of the presumptive test is challenged.

Figure 5:
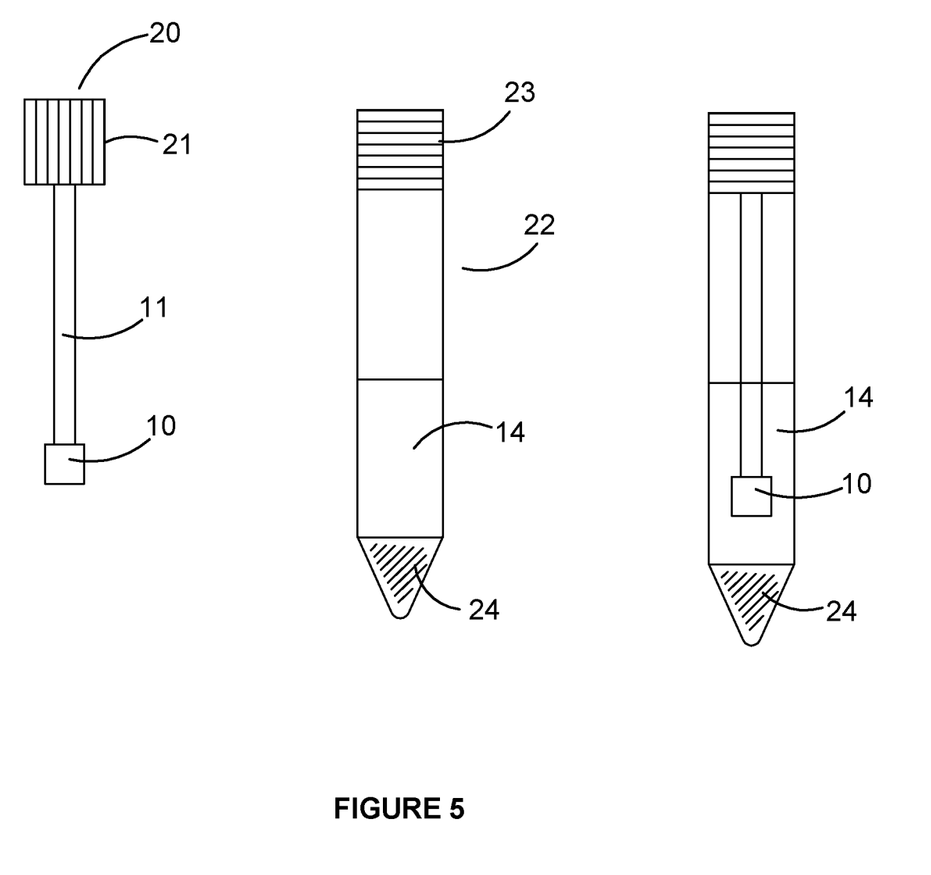
FIG. 5 shows kits or devices suitable for the detection of the colour change.

A particular embodiment of the test kit is shown in FIG. 5. A collection swab 20 has an absorbent end section 10 which can be used to collect particles of the suspected drug material for collection. The absorbent portion 10 is mounted on an elongate shaft 11 which connects to the inside of a tube lid 21. In use, the absorbent end of the swab is inserted into the tube 22 and the tube lid 21 is sealingly engaged with the tube, e.g. by means of interlocking threads 23. The tube 22 contains the necessary aqueous reagents 14 and a dense organic layer 24. Upon sealing engagement, the absorbent portion 10 contacts the aqueous reagents 14 and the complexation begins, thereby developing the necessary colour, which extracts into the organic layer 24. The tube desirably has a reduced cross section at the lower portion to enable better examination of a small amount of solvent.

The lower tip shown in FIG. 5 is conical, although this is not a necessary condition and in many cases it is preferred that the reduced path has a lower portion of reduced cross section with a constant profile. A lower portion of reduced but constant square cross section for example may be more amenable for use in instrumental analysis.

It was noted that the order of addition of catalyst, cathinone, or neocuproine had no effect upon the final colour produced by the test. The relative amounts of the compounds were also found, within reason, not to impact on the outcome of the test. It is important to bear in mind that in the field, the amount of seized material tested, and the relative amount of cathinone contained therein will not be known with any precision. Field tests need to be quite robust and relatively insensitive to the exact amount of drug. The methods of the present invention are suitably robust and in general, the tests can be carried out using rough or approximate quantities of drug and reagent without obtaining a materially different test outcome.

The amount of the drug used or contained within the sample does however affect the time for the colour change to occur.

Also, a very large excess of neocuproine relative to copper resulted in inherent colour changes prior to contact with ant potential drug containing sample. However, those skilled in the art will readily be aware of the unsuitability of a coloured pre-prepared reagent prior to attempting any testing.

A porcelain well plate containing a neocuproine solution and copper II was treated with a sample of cathinone at environmental temperature. No colour change was detectable. A small amount of catalyst was then added and the mixture further observed for a short time, whereupon the distinctive yellow orange colour of the cathinone neocuproine complex was observed.

Similarly, a porcelain well plate containing a small amount of catalyst was treated with a sample of cathinone at environmental temperature. No colour change was detectable. A small amount of neocuproine was then added and the mixture further observed for a short time, whereupon the distinctive yellow orange colour of the cathinone neocuproine complex was again observed.

It was found that the test could be simplified significantly by combining the reagents together in a single test formulation. The three reagents: copper(II) nitrate, neocuproine and sodium acetate were combined into one solution in the ratio 5:2:2 molar ratio, respectively. This test solution was used on several drug samples and afforded results identical to those from adding the reagents sequentially. In addition, it was found that the test solution was effective for at least several months after preparation.

A potential drawback of any test that relies upon inspection by the naked eye is that there can be numerous factors impacting upon what would be considered to constitute a determinative colour change. This can be particularly challenging in the case of field tests for drugs where the lighting conditions and stresses on the analyst would generally be much less favourable than those in the laboratory. Instrumental analysis can help overcome this potential problem.

Figure 6:
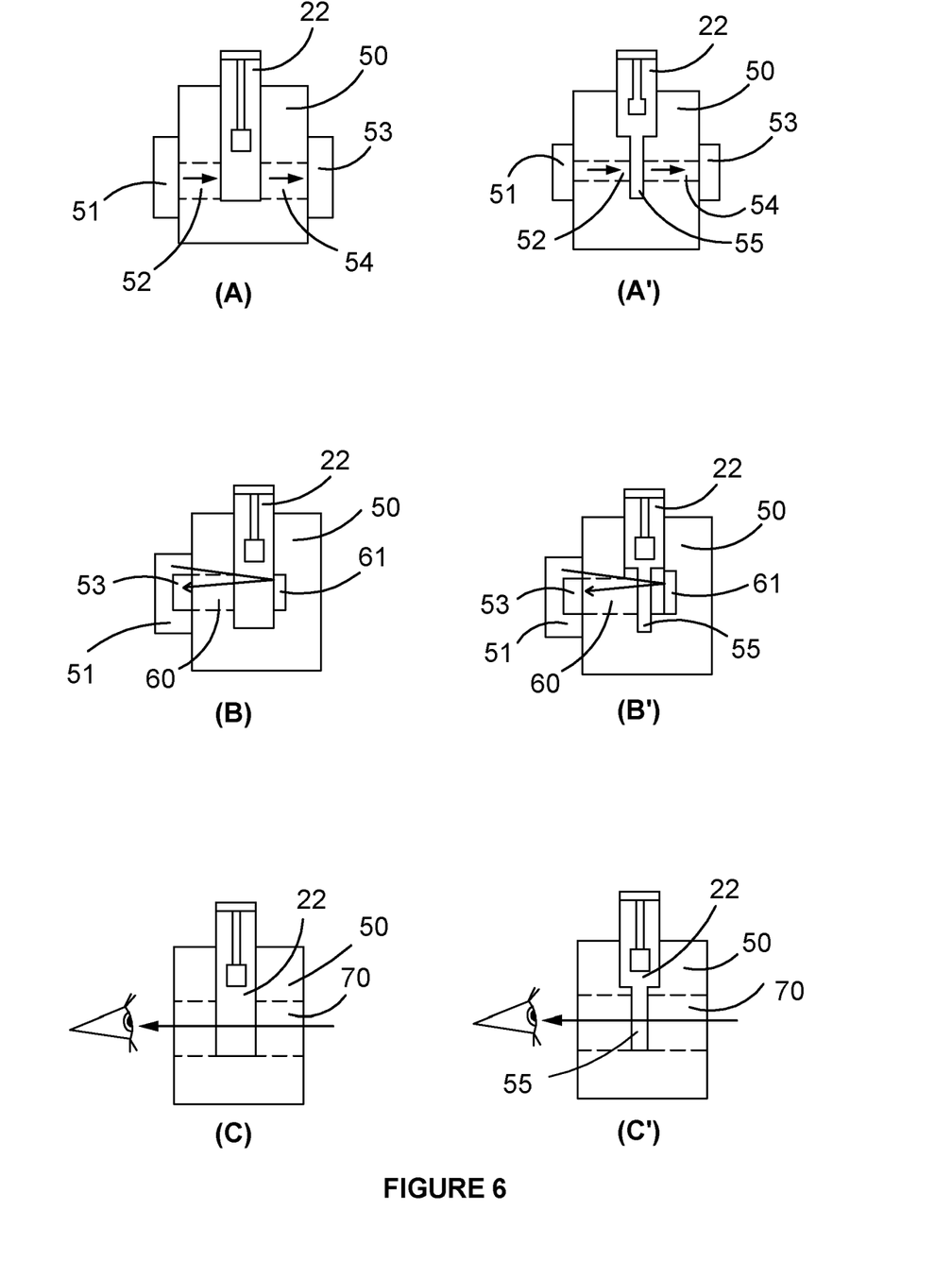
FIG. 6 shows a variety of exemplary configurations of devices of the present invention

Non-limiting examples of some colorimetric analysis devices envisaged to be suitable for carrying out the tests of the present invention are shown in FIG. 6. In all the embodiments shown, the device 50 has a cavity designed to hold a sample tube 22 and an inspection window or windows configured to allow spectroscopic analysis of a relevant coloured section of the material contained in the tube. The cavity is configured so as to generally occlude the rest of the tube apart from the inspection window or windows. This functions so as to provide controlled light conditions inside the device.

The specific device in 6A and 6A' has two opposed windows to allow a light from a light source 51 to enter from a first window 52 and exit to a detector 53 at an opposed window 54. The detector could be any sort of visible detector, or even a simple RGB detector. In FIG. 6A, the tube 22 is of continuous cross section, whereas in 6A', it is of reduced cross section 55 at its lower end to accommodate the heavy organic phase with increased concentration of the coloured complex.

Alternatively, the device as shown in 6B and 6B' could have a single window 60 with an opposed reflective portion, where the light enters and exits via the same window 60, after passing twice through the sample, before entering detector 53. 6B' also has a region of reduced cross section 55.

Alternatively, the device as shown in 6C and 6C' could be configured for hand held use. The device has a through passage 70 to enable visual inspection of the tube 22 (or reduced portion 55) without interference. Light passing through the sample is simply observed with the naked eye. This embodiment could advantageously contain a reference sample for side-by side comparison.

Colorimetric devices according to the present invention can be made in portable or mobile form, and the accompanying software can be configured to analyse the output of the RGB or other detector and provide simply a positive or negative result for the presence of a cathinone.

Figure 7:
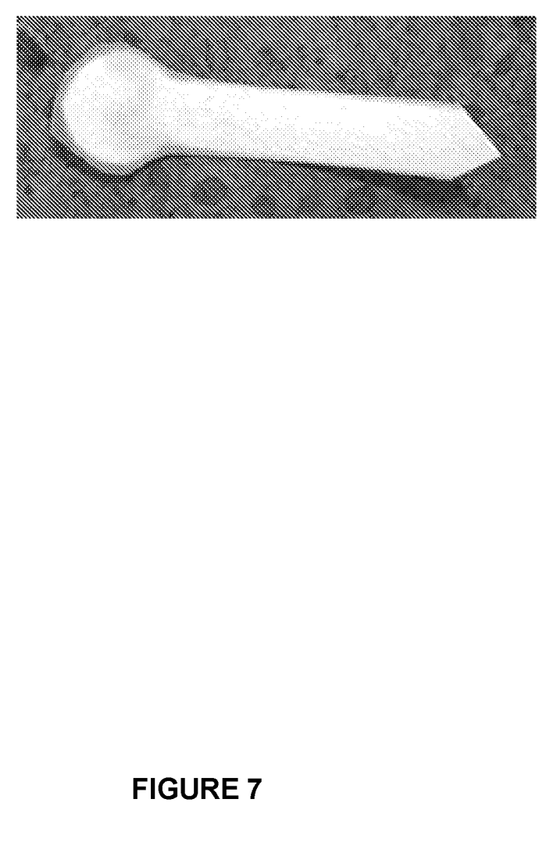
FIG. 7 shows a paper based device for detecting cathinones

The present invention is also amenable to use in the form of a paper-based microfluidic test device. A strip of filter paper was spotted with 5, 2, 2 µL of each copper nitrate (5.0 mM), neocuproine (5.0 mM) and sodium acetate (2M) solutions. The strip was allowed to dry. The dry strip was then dipped into a solution containing 4MMC, (4-methyl-methcathinone). Exposure of the strip to mild warming led to development of a coloured spot characteristic of a cathinone moiety. The colour was clearly detectable after ten minutes. FIG. 7 shows the results of a positive cathinone test on a paper strip. A blank sample showed no such colour change.

The use of the strip in conjunction with a colorimetric detector would facilitate detection of the coloured complex indicative of cathinone in a short time. Such a test can be readily used for example in hospitals to screen for drugs (as part of an array of tests to diagnose potential overdoses) or as a part of a sport or work based drug testing policy, where the speed and simplicity of a presumptive test are desirable, but where a rapid conclusion is not essential.

As well as strips, the test would be amenable on other solid supports, such as beads.

It was also found possible to prepare the reagents in the form of a single part solution. The three reagents: copper nitrate, neocuproine and sodium acetate were combined into one solution in the ratio 5:2:2, respectively. This test solution was used on several drug samples and afforded results identical to those from adding the reagents sequentially.

This single-part test solution was found to remain effective months after preparation. The use of a single-part solution will make the test method significantly simpler to use in the field.

It is known that after ingestion cathinone is partially excreted in the urine in unmetabolised form. Accordingly, the methods of the present invention, due to their selectivity and sensitivity are useful in detecting cathinone post use, where no trace of the undigested material is present.

A sample of blood, urine or saliva is subjected to the test methodology described above where a layer of organic solvent such as chloroform is included. The reaction to form the copper(I)-neocuproine takes place as described above and the coloured complex, where present, moves into the organic layer where it can be visually detected. The application of a test under such circumstances is qualitative however, it is highly useful as a rapid presumptive test particularly if a drug overdose is suspected.

The test of the present invention can be used in a standalone form, for cathinones only, but it is envisaged that it may be beneficial to employ the test as part of a kit of multiple distinct tests for various specific individual illicit substances. In this way, an unidentified sample can be subjected in parallel to many tests seeking to make a presumptive identification.

EXPERIMENTAL

In one particular non-limiting embodiment, the test is as follows:

A few crystals of the drug material are placed into a micro test tube. A combined reagent solution is added. The combined reagent solution contains three aqueous reagent solutions, copper(II) 5.0 mM, in the form of copper nitrate, neocuproine (5.0 mM) and sodium acetate (2M) in a 5:2:2 ratio. Chloroform (5 drops, about 0.25 ml) is added. Approximately 0.5 mg of salt is added. The tube is then shaken or flicked to allow adequate mixing.

The colour change is then observed—a good colour change was observed after 2 minutes, allowing for confirmation of the presence of cathinone moieties.

A number of synthetic cathinones were prepared and tested in the embodiments of the present invention and the results showed that the catalytic and mechanical acceleration did not affect the usefulness of the presumptive neocuproine test. The results are shown in the table below. The range of substituents chosen was considered to represent a selection of the range of substituents most commonly encountered in illicit seizures.

| Compound name | Structure | Preparation method summary |
| --- | --- | --- |
| 4-methylmethcathinone HCl | | Alpha bromination<br>Amination with methylamine<br>Conversion to HCl salt |
| 4-fluoromethcathinone HCl | | Alpha bromination<br>Amination with methylamine<br>Conversion to HCl salt |
| 4-methylethcathinone HCl | | Alpha bromination<br>Amination with ethylamine<br>Conversion to HCl salt |
| Methylone HCl | | Grignard reaction with EtMgCl<br>Oxidation<br>Alpha bromination<br>Amination with methylamine<br>Conversion to HCl salt |
| Butylone HCl | | Grignard reaction with PrMgCl<br>Oxidation<br>Alpha bromination<br>Amination with methylamine<br>Conversion to HCl salt |
| Pentylone HCl | | Grignard reaction with BuMgCl<br>Oxidation<br>Alpha bromination<br>Amination with methylamine<br>Conversion to HCl salt |
| Pyrovalerone HCl | | Grignard reaction with BuMgCl<br>Oxidation<br>Alpha bromination<br>Amination with pyrrolidine<br>Conversion to HCl salt |

-continued

| Compound name | Structure | Preparation method summary |
| --- | --- | --- |
| Methcathinone HCl | | Oxidation<br>Conversion to HCl salt |
| 3,4-methylenedioxy-pyrovalerone | | Grignard reaction with BuMgCl<br>Oxidation<br>Alpha bromination<br>Amination with pyrrolidine<br>Conversion to HCl salt |
| a-pyrrolidinovalero-phenone HCl | | Grignard reaction with BuMgCl<br>Oxidation<br>Alpha bromination<br>Amination with pyrrolidine<br>Conversion to HCl salt |
| 4-methylpyrrolidino-propiophenone HCl | | Grignard reaction with EthMgCl<br>Oxidation<br>Alpha bromination<br>Amination with pyrrolidine<br>Conversion to HCl salt |

The invention claimed is:

1. A method of detecting the presence of a cathinone moiety in a sample, the method comprising the steps of contacting the sample with a solution comprising neocuproine, a source of copper(II) and an alkali metal catalyst to catalyse the formation of a cathinone neocuproine complex and observing a colour change, where present, that correlates with the presence of cathinone, and wherein the method takes place at environmental temperature.

2. The method according to claim 1 wherein the colour change is observed at environmental temperature within 10 minutes.

3. The method according to claim 1 wherein the colour change is observed at environmental temperature within 5 minutes.

4. The method according to claim 1 wherein the colour change is observed at environmental temperature within 2 minutes.

5. The method according to claim 1 wherein the solution is an aqueous solution.

6. The method according to claim 1 wherein the buffer is a mildly acidic buffer to keep pH in the range 3-6.

7. The method according to claim 6 wherein the sample, the neocuproine, the source of copper(II), the catalyst and the buffer are added in any order.

8. The method according to claim 1 wherein the neocuproine, the source of copper(II) and the buffer are added simultaneously.

9. The method according to claim 1 wherein the source of copper(II) is copper nitrate.

10. The method according to claim 1 wherein the buffer is sodium acetate.

11. The method according to claim 1 wherein the catalyst is selected from the group consisting of lithium fluoride, potassium fluoride, and potassium chloride.

12. The method according to claim 1 wherein the catalyst is selected from the group consisting of lithium fluoride, and potassium chloride.

13. A method of detecting the presence of a cathinone moiety in a sample, the method comprising the steps of:
  i. contacting the sample with a solution comprising neocuproine, a source of copper(II), an alkali metal halide catalyst to catalyse the formation of a cathinone neocuproine complex and a plurality of mechanical elements;
  ii. agitating the mechanical elements to provide friction therebetween and observing a colour change, where present, that correlates with the presence of cathinone, and wherein the method takes place at environmental temperature.

14. A method according to claim 13 wherein the mechanical elements are beads.

15. The method according to claim 14 wherein the beads are selected from the group consisting of glass beads, polyethylene balls and polyvinyl acetate spheres and silica gel particles.

16. A method according to claim 13 when carried out in a malleable container.

17. The method according to claim 13 wherein the catalyst is selected from the group consisting of lithium fluoride, potassium fluoride, and potassium chloride.

* * * * *